US011511044B2

(12) United States Patent
Oda et al.

(10) Patent No.: US 11,511,044 B2
(45) Date of Patent: Nov. 29, 2022

(54) SEQUENCED SYRINGE ASSEMBLY

(71) Applicant: CareFusion 303, Inc., San Diego, CA (US)

(72) Inventors: Todd Oda, Torrance, CA (US); George Mansour, Diamond Bar, CA (US); Eugene Mason, La Habra Heights, CA (US); Tomas Frausto, Walnut, CA (US); Dylan Beyhl, Scottsdale, AZ (US)

(73) Assignee: CareFusion 303, Inc., San Diego, CA (US)

( * ) Notice: Subject to any disclaimer, the term of this patent is extended or adjusted under 35 U.S.C. 154(b) by 224 days.

(21) Appl. No.: 16/572,379

(22) Filed: Sep. 16, 2019

(65) Prior Publication Data

US 2021/0077734 A1    Mar. 18, 2021

(51) Int. Cl.
*A61M 5/31*    (2006.01)
*A61M 5/145*   (2006.01)
*A61M 5/19*    (2006.01)
*A61M 5/315*   (2006.01)
*A61M 5/14*    (2006.01)

(52) U.S. Cl.
CPC ...... *A61M 5/3146* (2013.01); *A61M 5/14546* (2013.01); *A61M 5/19* (2013.01); *A61M 5/31515* (2013.01); *A61M 5/31596* (2013.01); *A61M 2005/1402* (2013.01); *A61M 2005/3152* (2013.01)

(58) Field of Classification Search
CPC ............ A61M 5/19; A61M 2005/3152; A61M 2005/31598; A61M 5/31595
See application file for complete search history.

(56) References Cited

U.S. PATENT DOCUMENTS

| 2007/0016144 | A1* | 1/2007 | Sibbitt, Jr. | ......... A61M 5/31511 604/218 |
| 2007/0060894 | A1* | 3/2007 | Dai | .................... A61M 5/31511 604/207 |
| 2013/0267908 | A1 | 10/2013 | Leak et al. | |
| 2016/0263319 | A1* | 9/2016 | Brandeis | ................. A61M 1/67 |
| 2019/0321021 | A1* | 10/2019 | Guo | ..................... A61M 5/2422 |
| 2020/0129695 | A1* | 4/2020 | Brandeis | ................. A61M 1/81 |

FOREIGN PATENT DOCUMENTS

JP    2010075287 A    4/2010

OTHER PUBLICATIONS

International Search Report and Written Opinion for Application No. PCT/US2020/050752, dated Dec. 1, 2020, 17 pages.

* cited by examiner

*Primary Examiner* — Emily L Schmidt
(74) *Attorney, Agent, or Firm* — Morgan, Lewis & Bockius LLP

(57) ABSTRACT

Syringe assemblies are described herein. A syringe assembly includes an assembly housing, a first syringe, a second syringe, and a connecting gear. The first syringe is disposed within the assembly housing. Each plunger is movable within the respective syringe cavity and defines a respective chamber in the respective syringe cavity, wherein the respective chamber is in fluid communication with the respective syringe port, the respective plunger comprising a respective gear rack extending longitudinally along the respective plunger. The connecting gear is rotatably coupled to the assembly housing. The connecting gear is configured to be in meshed engagement with at least one of the first gear rack and the second gear rack of the syringes.

14 Claims, 9 Drawing Sheets

SEQUENCED SYRINGE ASSEMBLY

FIELD OF THE INVENTION

The present disclosure generally relates to medication delivery systems, and, in particular, to syringe assemblies.

BACKGROUND

Medical treatments often include the infusion of a medical fluid (e.g., a saline solution or a liquid medication) to patients using an intravenous (IV) catheter that is connected though an arrangement of flexible tubing and fittings, commonly referred to as an "IV set," to a source of fluid, for example, a bag or a syringe. Certain configurations of IV sets may have extended lengths of tubing, for example, in excess of 6 feet. Additionally, tubing may be primed with saline prior to the infusion of a liquid medication.

In some applications, during the use of IV catheters, saline from the priming process may be delivered to a patient before the liquid medication is delivered to the patient.

SUMMARY

The disclosed subject matter relates to syringe assemblies. In certain embodiments, a syringe assembly is disclosed that comprises an assembly housing; a first syringe disposed within the assembly housing, the first syringe comprising: a first syringe body defining a first syringe cavity and a first syringe port, wherein the first syringe port is in fluid communication with the first syringe cavity; and a first plunger movable within the first syringe cavity and defining a first chamber in the first syringe cavity, wherein the first chamber is in fluid communication with the first syringe port, the first plunger comprising a first gear rack extending longitudinally along the first plunger; a second syringe disposed within the assembly housing, the second syringe comprising: a second syringe body defining a second syringe cavity and a second syringe port, wherein the second syringe port is in fluid communication with the second syringe cavity; and a second plunger movable within the second syringe cavity and defining a second chamber in the second syringe cavity, wherein the second chamber is in fluid communication with the second syringe port, the second plunger comprising a second gear rack extending longitudinally along the second plunger; and a connecting gear rotatably coupled to the assembly housing, wherein the connecting gear is configured to be in meshed engagement with at least one of the first gear rack and the second gear rack.

In certain embodiments, a method to deliver medication is disclosed that comprises advancing a medication plunger to urge medication through a delivery flow path of a tubing; and rotating a connecting gear by advancing the medication plunger, wherein the medication plunger includes a medication gear rack in meshed engagement with the connecting gear.

In certain embodiments a medication delivery system is disclosed that comprises a syringe assembly, comprising: an assembly housing; a first syringe disposed within the assembly housing, the first syringe comprising: a first syringe body defining a first syringe cavity and a first syringe port, wherein the first syringe port is in fluid communication with the first syringe cavity; and a first plunger movable within the first syringe cavity and defining a first chamber in the first syringe cavity, wherein the first chamber is in fluid communication with the first syringe port, the first plunger comprising a first gear rack extending longitudinally along the first plunger; a second syringe disposed within the assembly housing, the second syringe comprising: a second syringe body defining a second syringe cavity and a second syringe port, wherein the second syringe port is in fluid communication with the second syringe cavity; and a second plunger movable within the second syringe cavity and defining a second chamber in the second syringe cavity, wherein the second chamber is in fluid communication with the second syringe port, the second plunger comprising a second gear rack extending longitudinally along the second plunger; and a connecting gear rotatably coupled to the assembly housing, wherein the connecting gear is configured to be in meshed engagement with at least one of the first gear rack and the second gear rack; and a tubing defining a first flow path and a second flow path, wherein the first flow path is in fluid communication with the first syringe port, and the second flow path is in fluid communication with the second syringe port.

It is understood that various configurations of the subject technology will become readily apparent to those skilled in the art from the disclosure, wherein various configurations of the subject technology are shown and described by way of illustration. As will be realized, the subject technology is capable of other and different configurations and its several details are capable of modification in various other respects, all without departing from the scope of the subject technology. Accordingly, the summary, drawings and detailed description are to be regarded as illustrative in nature and not as restrictive.

BRIEF DESCRIPTION OF THE DRAWINGS

The accompanying drawings, which are included to provide further understanding and are incorporated in and constitute a part of this specification, illustrate disclosed embodiments and together with the description serve to explain the principles of the disclosed embodiments. In the drawings.

DETAILED DESCRIPTION

The disclosed syringe assembly incorporates multiple syringes with a connecting gear to actuate the syringes. The syringe assembly can control the advancing and retracting of the syringes to control the fluid flow to and from each of the syringes. By controlling the fluid flow to and from each of the syringes, the priming and delivery of medication and other medical fluids can be simplified.

The detailed description set forth below is intended as a description of various configurations of the subject technology and is not intended to represent the only configurations in which the subject technology may be practiced. The detailed description includes specific details for the purpose of providing a thorough understanding of the subject technology. However, it will be apparent to those skilled in the art that the subject technology may be practiced without these specific details. In some instances, well-known structures and components are shown in block diagram form in order to avoid obscuring the concepts of the subject technology. Like components are labeled with identical element numbers for ease of understanding. Reference numbers may have letter suffixes appended to indicate separate instances of a common element while being referred to generically by the same number without a suffix letter.

While the following description is directed to the administration of medical fluid using the disclosed syringe assembly, it is to be understood that this description is only an example of usage and does not limit the scope of the claims. Various aspects of the disclosed syringe assembly may be used in any application where it is desirable to provide for the administration of medical fluids.

The disclosed syringe assembly overcomes several challenges discovered with respect to certain conventional syringes. One challenge with certain conventional syringes is that syringes may deliver excess medical fluid, such as saline, to patients. Further, conventional syringes may require manual advancing and retraction in sequence. Because excess medical fluid may delay the delivery of medical fluids, may not be tolerated by fluid restricted patients, such as premature babies, and manual operation of conventional syringes may be subject to error, the use conventional syringes is undesirable.

Therefore, in accordance with the present disclosure, it is advantageous to provide a syringe assembly as described herein that eliminates or substantially reduces delivering excess medical fluid to a patient and simplifies the operation of the syringes. The disclosed syringe assembly provides a gear mechanism that permits simplified operation while reducing excess medical fluid delivered to the patient.

An example of a syringe assembly that prevents delivery of excess medical fluid is now described.

Figure 1:
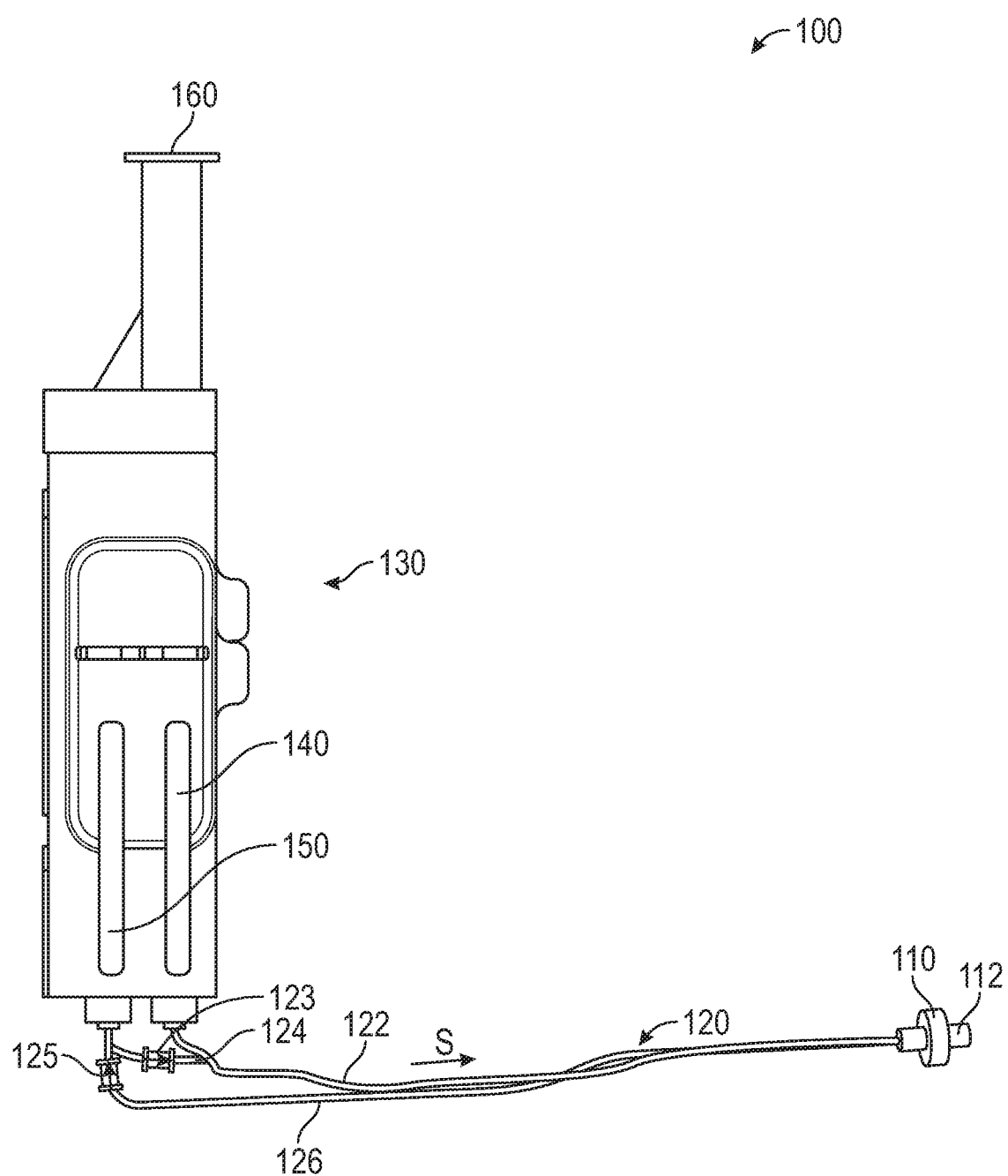
FIG. 1 is an elevation view of a medication delivery system, in accordance with various aspects of the present disclosure.

FIG. 1 is an elevation view of a medication delivery system 100, in accordance with various aspects of the present disclosure. In the illustrated example, the medication delivery system 100 delivers medication from a syringe assembly 130 to the patient via a catheter 112 without delivering excess fluid, such as saline, used to prime the medication delivery system 100.

In some embodiments, a delivery flow path 122 of a dual lumen tubing 120 can be primed with saline to remove any air or trapped gasses with the delivery flow path 122 of the dual lumen tubing 120. Saline can be advanced from the syringe assembly 130, through the delivery flow path 122 and to the valve 110.

In a priming configuration, the valve 110 can prevent from the delivery flow path 122 from entering the patient catheter 112 and can instead direct the saline toward the return flow path 126 to allow the primed saline to be returned to the syringe assembly 130.

Figure 2:
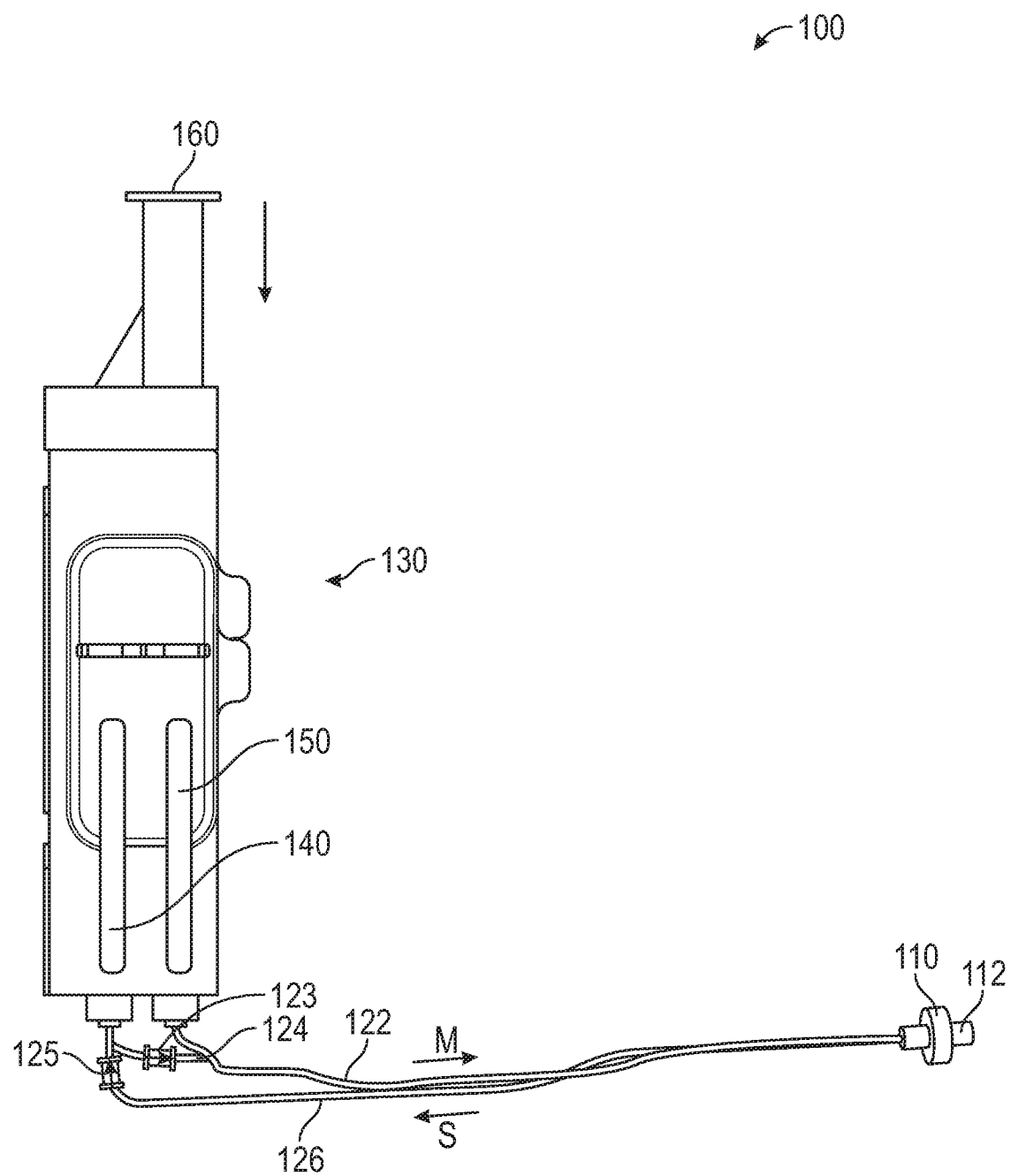
FIG. 2 is an elevation view of the medication delivery system of FIG. 1, with the pusher assembly depressed, in accordance with various aspects of the present disclosure.

FIG. 2 is an elevation view of the medication delivery system 100 of FIG. 1, with the pusher assembly 160 depressed, in accordance with various aspects of the present disclosure. In the illustrated example, the syringe assembly 130 advances medication within the delivery flow path 122 to prime the delivery flow path 122. Advantageously, by priming the delivery flow path 122 with medication, the medication can be delivered to the patient via the catheter 112 proximal to the patient with less delay and without delivering the saline used to prime the delivery flow path 122.

To introduce medication into the delivery flow path 122, the pusher assembly 160 can be advanced or otherwise displaced to introduce a volume of medication into the delivery flow path 122 of the dual lumen tubing 120. In some embodiments, the advancement of the pusher assembly 160 can actuate a medication syringe 150 disposed within the syringe assembly 130. Optionally, the medication syringe 150 can be configured to be advanced or displaced a desired amount to dispense a volume of medication into the delivery flow path 122 that is equivalent to the volume of the delivery flow path 122. In other words, medication syringe 150 can be advanced to fill the volume of the delivery flow path 122 up to the valve 110 to prime the medication for administration via the catheter 112.

In some embodiments, the priming of medication into the delivery flow path 122 can be signaled, controlled, or otherwise simplified. For example, the syringe assembly 130 can include an internal mechanism that limits travel or provides a tactile signal to a clinician when the delivery flow path 122 is primed. In some embodiments, the limit or signal is calibrated to the volume of the delivery flow path 122. By providing a travel limit or signal during priming, a desired volume of medication can be introduced into the delivery flow path 122, for example, a sufficient medication volume to fill the delivery flow path 122.

As illustrated, as the medication is introduced into the delivery flow path 122, the saline previously primed through the delivery flow path 122 is displaced. The displaced saline is directed by the valve 110 into the return flow path 126.

Medical fluid from the return flow path 126 can be returned into the syringe assembly 130. Returned medical fluid such as saline can be introduced into a return or saline syringe 140 of the syringe assembly 130. In some embodiments, the return flow path 126 includes a check valve 125 to prevent the backflow of medical fluid from the saline syringe 140 into the dual lumen tubing 120.

Figure 3:
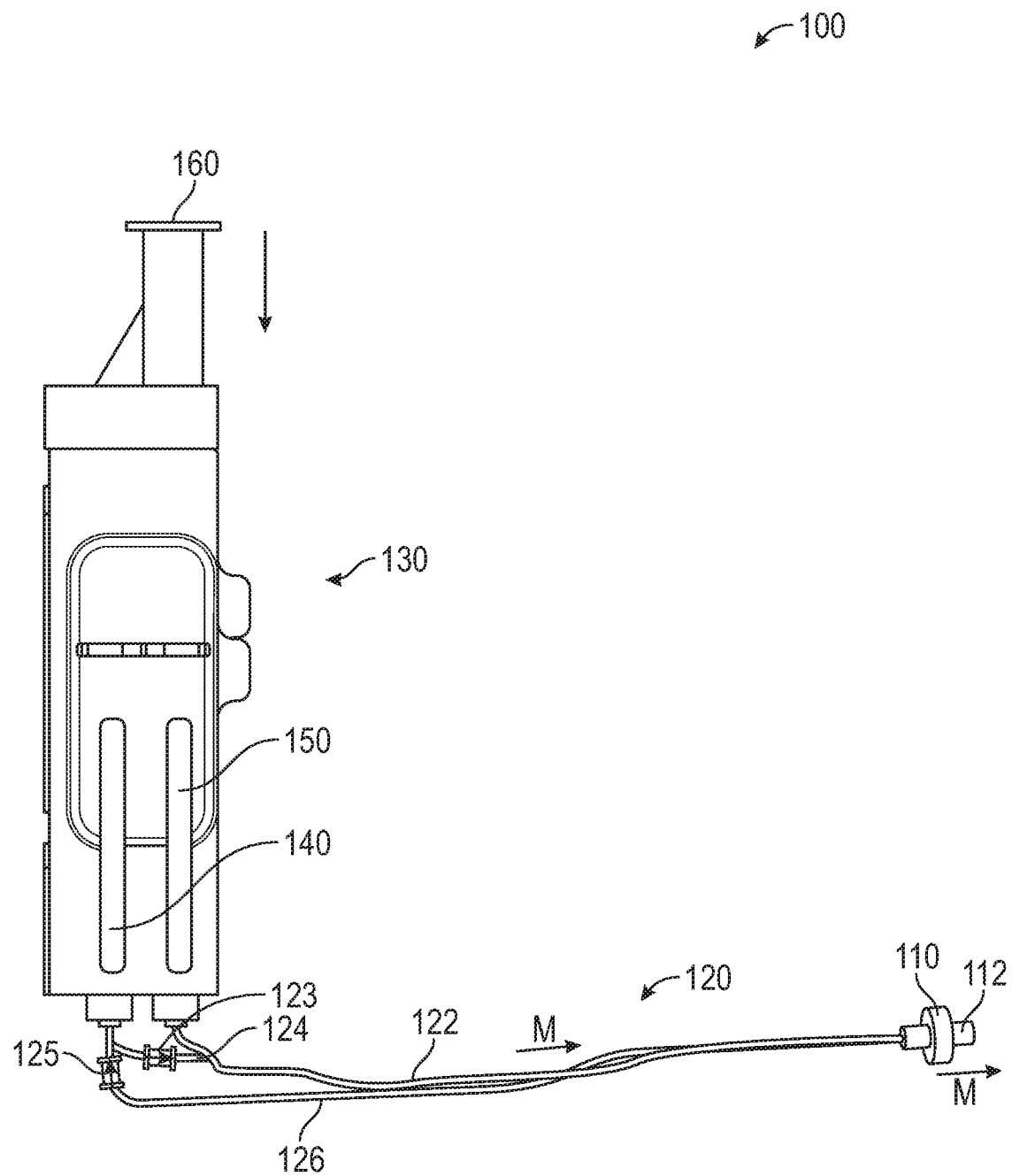
FIG. 3 is an elevation view of the medication delivery system of FIG. 1, with the pusher assembly further depressed, in accordance with various aspects of the present disclosure.

FIG. 3 is an elevation view of the medication delivery system 100 of FIG. 1, with the pusher assembly 160 further depressed, in accordance with various aspects of the present disclosure. In the illustrated example, the syringe assembly 130 is actuated to dispense medication to the patient through the catheter 112.

As illustrated, the pusher assembly 160 can be further advanced to actuate the medication syringe 150 within the syringe assembly 130. By actuating the pusher assembly 160, the medication syringe 150 can be advanced to deliver medication from the syringe assembly 130 into the delivery flow path 122. In some embodiments, the syringe assembly 130 can be actuated by a syringe pump to control the flow of medication to the patient. As can be appreciated, the syringe pump can be configured to include a priming sequence with an increased pump rate to rapidly prime the delivery flow path 122.

During operation, the valve 110 is actuated to permit the flow of medication from the delivery flow path 122 to the patient via the catheter 112. In some embodiments, the fluid pressure within the delivery flow path 122 can exceed the cracking pressure of the valve 110 to allow flow to the catheter 112. The valve 110 can be located proximal to the patient to minimize the length of the catheter 112, which reduces the amount of saline administered to the patient, and reduces the delivery time for the medication.

Figure 4:
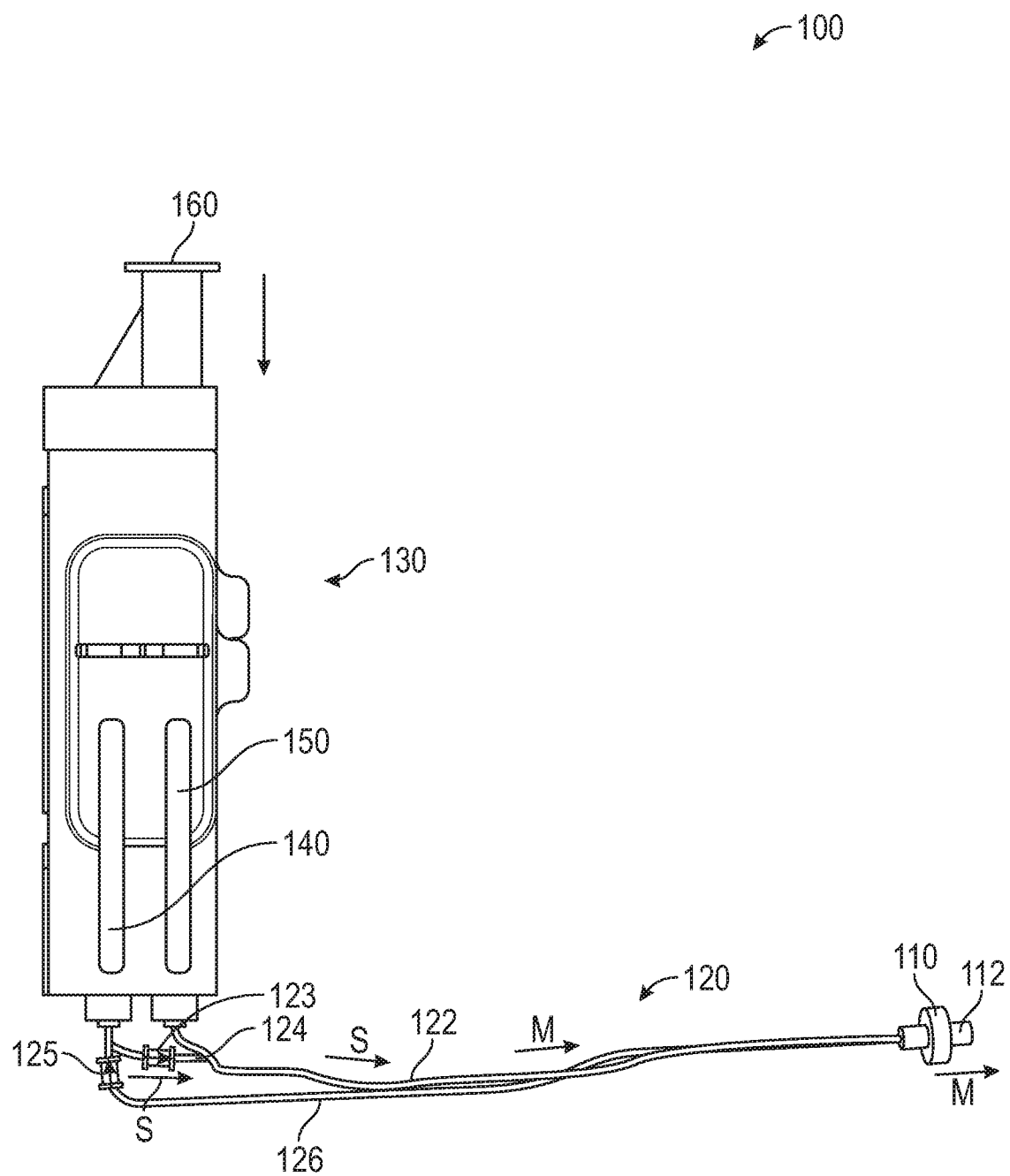
FIG. 4 is an elevation view of the medication delivery system of FIG. 1, with the pusher assembly further depressed, in accordance with various aspects of the present disclosure.

FIG. 4 is an elevation view of the medication delivery system 100 of FIG. 1, with the pusher assembly 160 further depressed, in accordance with various aspects of the present disclosure. In the illustrated example, the syringe assembly 130 advances saline through the delivery flow path 122 to advance the remaining medication to the patient via the catheter 112.

As illustrated, after the medication is expelled from the medication syringe 150, medication may remain in the volume of the delivery flow path 122. To ensure that the medication is fully delivered to the patient, the pusher assembly 160 can be further advanced to administer a saline "push" from the saline syringe 140 to continue to advance the medication through the delivery flow path 122 after the medication within the medication syringe 150 is exhausted. Saline can be administered through the delivery flow path 122 until the medication is fully administered to the patient. As illustrated, the saline from the saline syringe 140 can enter the delivery flow path 122 via the saline delivery line 124. The saline delivery line 124 can include a check valve 123 to prevent the backflow of medication or other medical fluids into the syringe assembly 130.

Figure 5:
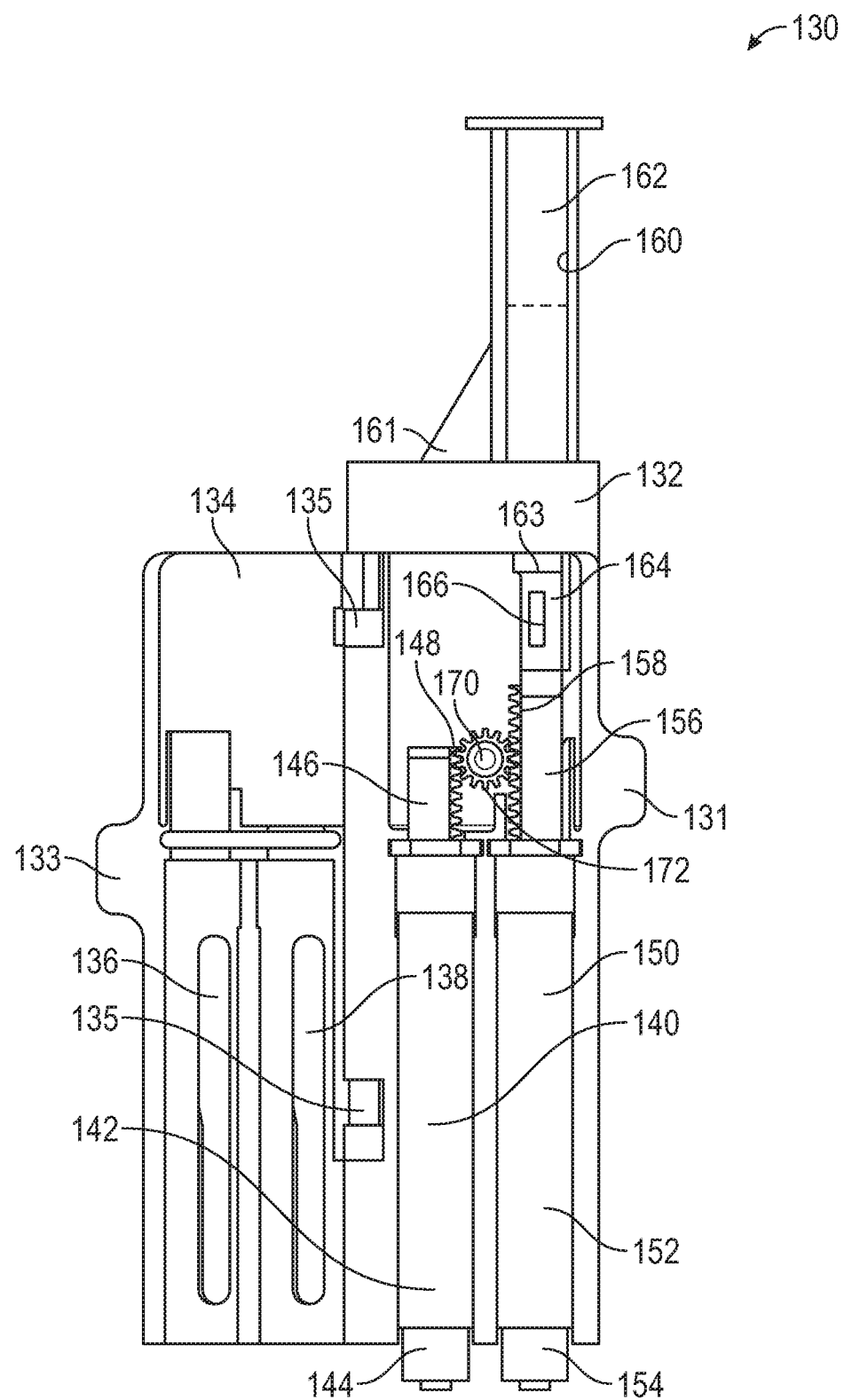
FIG. 5 is an elevation view of a syringe assembly, in accordance with various aspects of the present disclosure.

FIG. 5 is an elevation view of a syringe assembly 130, in accordance with various aspects of the present disclosure. In the illustrated embodiment, the syringe assembly 130 controls the flow of medication from the medication syringe 150 and the flow of saline from the saline syringe 140.

As illustrated, the medication syringe 150 can receive, store, and/or dispense medication in a medication cavity 152. In the illustrated embodiment, a medication plunger 156 is movable within the medication cavity 152 to define a medication chamber therein. The volume of the medication chamber is preferably defined by the position of the medication plunger 156 relative to the medication cavity 152. In some embodiments, the volume of the medication chamber is in fluid communication with the medication port 154. Embodiments of the medication syringe 150 can be commercially available, premade, prefilled, or otherwise adapted for use with the syringe assembly 130.

In some embodiments, the medication plunger 156 can be drawn distally to expand the medication chamber and draw in more medication or medical fluid through the medication port 154. During operation, the medication plunger 156 can be advanced proximally to contract the medication chamber and expel medication or medical fluids from the medication chamber through the medication port 154.

Similarly, the saline syringe 140 can receive, store and/or dispense saline in a saline cavity 142. The saline syringe 140 can store any other medical fluid, including medicine to allow the syringe assembly 130 to dispense multiple medications in sequence or simultaneously. In the illustrated embodiment, a saline plunger 146 is movable within the saline cavity 142 to define a saline chamber therein. The volume of the saline chamber is preferably defined by the position of the saline plunger 146 relative to the saline cavity 142. In some embodiments, the volume of the saline chamber is in fluid communication with the saline port 144. Embodiments of the saline syringe 140 can be commercially available, premade, prefilled, or otherwise adapted for use with the syringe assembly 130.

During operation, the saline plunger 146 can be drawn distally to expand the saline chamber and draw in more saline or medical fluid through the saline port 144. In some embodiments, the saline plunger 146 can be advanced proximally to contract the saline chamber and expel saline or medical fluids from the saline chamber through the saline port 144.

As illustrated, the saline syringe 140 and the medication syringe 150 can be housed within an assembly housing 132. The assembly housing 132 can include alignment and retention features to locate the saline syringe 140 and the medication syringe 150. The assembly housing 132 can include a cover 134 to retain and cover the components of the syringe assembly 130. The cover 134 can rotate on hinges 135 to close and cover the syringe assembly 130. Tabs 131, 133 formed on assembly housing 132 and the cover 134 can respectively facilitate in the opening and closing of the cover 134 for access to the saline syringe 140 and the medication syringe 150. The cover 134 can include a saline window 138 and a medication window 136 to allow a clinician to monitor the fluid level of the saline syringe 140 and the medication syringe 150, respectively.

In the depicted example, the syringe assembly 130 controls the actuation of the medication plunger 156 and the saline plunger 146 to facilitate the priming and administration of medication to a patient. In the depicted example, the syringe assembly 130 includes a pusher assembly 160 to advance the medication plunger 156 and/or the saline plunger 146. For example, by advancing the pusher assembly 160, the medication plunger 156 and the saline plunger 146 can be actuated in sequence to prime the medication delivery device, deliver medication, and provide a saline "push" to deliver any medication remaining in the delivery flow path.

Figure 6:
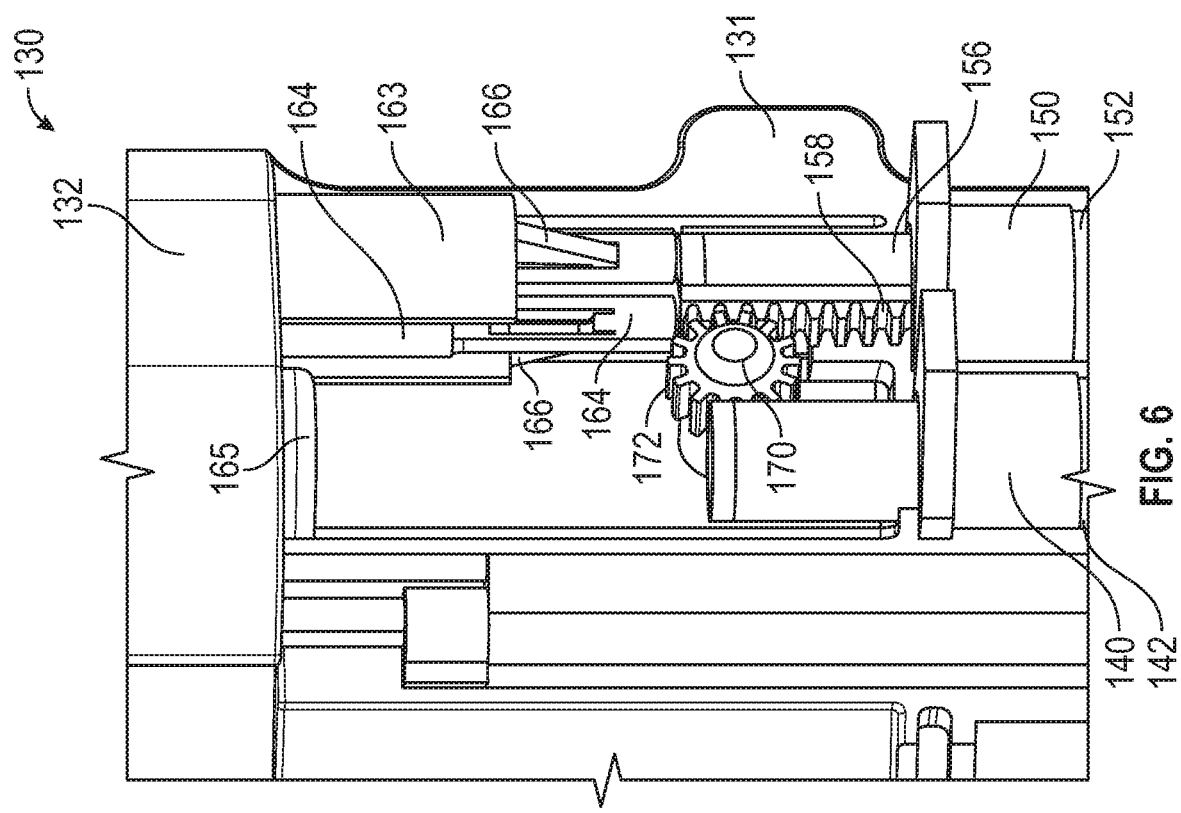
FIG. 6 is a perspective detail view of the syringe assembly of FIG. 5, in accordance with various aspects of the present disclosure.

FIG. 6 is a perspective detail view of the syringe assembly 130 of FIG. 5, in accordance with various aspects of the present disclosure. With reference to FIGS. 5 and 6, in the illustrated embodiment, the pusher assembly 160 includes a main pusher shaft 162 and an intermediate pusher shaft 164 configured to cooperatively advance the medication plunger 156 in response to the pusher assembly 160 being advanced. As illustrated, the intermediate pusher shaft 164 can extend at least partially from the main pusher shaft 162.

The intermediate pusher shaft 164 preferably is releasably coupled to the main pusher shaft 162 via a plurality of ears 166. In some embodiments, the ears 166 radially expand and engage against the main pusher shaft end 163 to prevent or limit the intermediate pusher shaft 164 from retracting into the main pusher shaft 162. During operation, as described herein, the ears 166 of the intermediate pusher shaft 164 can be radially retracted to allow the intermediate pusher shaft 164 to be retracted into the main pusher shaft 162, preventing or limiting advancement of the pusher assembly 160 from further actuating the medication plunger 156. In some embodiments, the ears 166 can be retracted by engaging with an activation tunnel 137 formed around the medication plunger 156.

Referring back to FIG. 5, the pusher assembly 160 includes a secondary pusher (not pictured in FIG. 5) extending laterally from the main pusher shaft 162 via a secondary pusher extension 161. The secondary pusher is configured to advance the saline plunger 146 in response to the pusher assembly 160 being advanced. The secondary pusher can be longitudinally offset from the intermediate pusher shaft 164, such that the intermediate pusher shaft 164 engages with the medication plunger 156 before the secondary pusher engages with the saline plunger 146 when the pusher assembly 160 is advanced. In some embodiments, the secondary pusher engages and advances the saline plunger 146 after the intermediate pusher shaft 164 has been disengaged from the main pusher shaft 162, allowing the pusher assembly 160 to be advanced to actuate the saline plunger 146 via the offset secondary pusher without further actuating the medication plunger 156.

Advantageously, during the administration of medication to patients, the pusher assembly 160 allows for medication to be dispensed from the medication syringe 150 by actuating the main pusher shaft 162 and the intermediate pusher shaft 164 and then allows for saline to be dispensed from the saline syringe 140 by actuating the secondary pusher.

In some embodiments, the syringe assembly 130 includes a priming mechanism to automate, control, or otherwise simplify the advancement of the medication plunger 156 and the retraction of the saline plunger 146 to facilitate the priming of medication into IV tubing. The priming mechanism is preferably configured to introduce a sufficient volume of medication from the medication syringe 150 into the IV tubing to fully fill or prime the IV line while removing any displaced liquid prior to the administration of medication to the patient.

In the illustrated embodiment, the priming mechanism includes a connecting gear 172 that effects retraction of the saline plunger 146 as the medication plunger 156 is advanced during a priming operation. In the depicted example, the medication plunger 156 includes a medication gear rack 158 extending longitudinally along the medication plunger 156. The medication gear rack 158 includes a plurality of teeth that can be in meshed engagement with the connecting gear 172. Similarly, the saline plunger 146 includes a saline gear rack 148 extending longitudinally along the saline plunger 146. The saline gear rack 148 includes a plurality of teeth that can also be in meshed engagement with the connecting gear 172.

Therefore, during a priming operation, as the medication plunger 156 is advanced by the pusher assembly 160 to administer medication, the medication gear rack 158 rotates the connecting gear 172 about the connecting gear shaft 170 in a clockwise direction. In response, the clockwise rotation of the connecting gear 172 retracts the saline plunger 146 in an opposite direction to draw in or receive saline from the IV tubing. As can be appreciated, the medication gear rack 158 and/or the saline gear rack 148 can be in meshed engagement with the connecting gear 172 before or during a priming operation and can be disengaged from the connecting gear 172 during other operations. Further, the length of the medication gear rack 158 and/or the saline gear rack 148 and the relative position of the medication plunger 156 and the saline plunger 146 can be configured to provide the desired operation.

As can be appreciated, features of the syringe assembly 130, such as the pusher assembly 160 and the priming mechanism including the connecting gear 172, the medication gear rack 158, and the saline gear rack 148 can be cooperatively utilized in the operation of the syringe assembly 130 to sequentially permit the priming of an IV line, the administration of medication to a patient, and providing the saline push of any remaining medication by advancing the pusher assembly 160.

Figure 7:
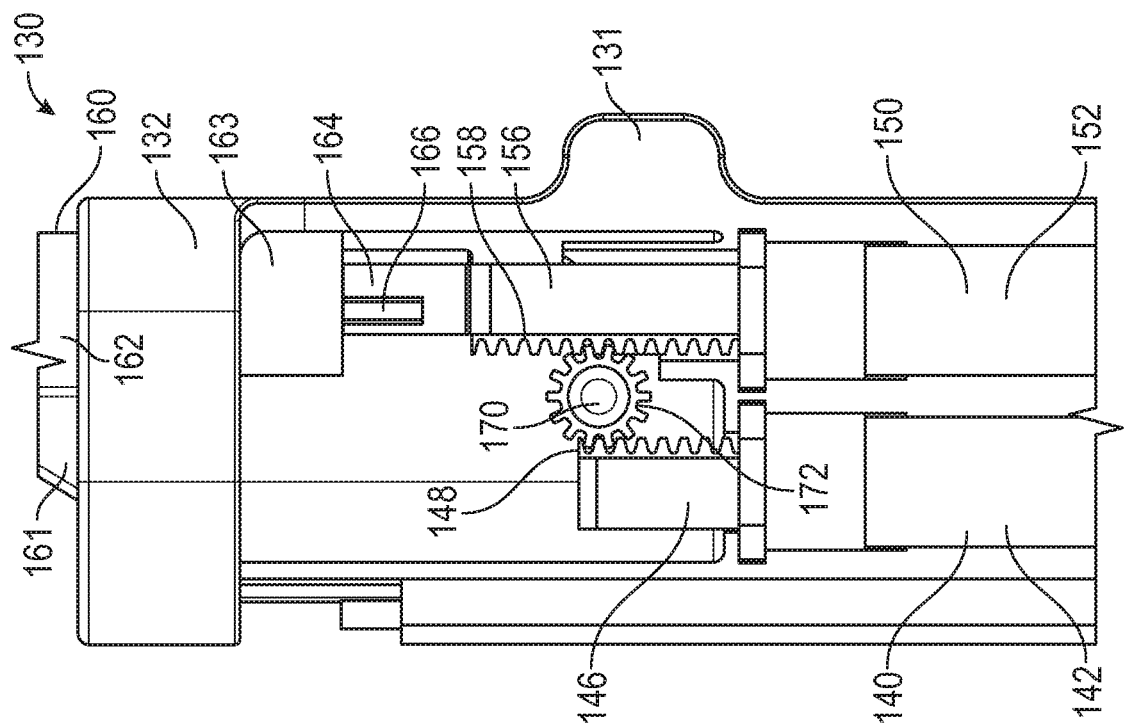
FIG. 7 is a detail view of the syringe assembly of FIG. 5 in a priming configuration, in accordance with various aspects of the present disclosure.

FIG. 7 is a detail view of the syringe assembly 130 of FIG. 5 in a priming configuration, in accordance with various aspects of the present disclosure. As described herein, by advancing the pusher assembly 160 from an initial position, an IV line can be primed with medication.

By advancing the pusher assembly 160, the main pusher shaft 162 and the intermediate pusher shaft 164 coupled thereto engage and advance the medication plunger 156. By advancing the medication plunger 156, medication from the medication syringe 150 can advance through the IV tubing and prime the IV tubing. As described herein, the medication plunger 156 can be advanced by a desired or predetermined amount corresponding to the IV tubing volume during the priming process.

As the medication is advanced through the IV tubing during priming, any fluid such as saline remaining in the IV tubing may be displaced. Therefore, the syringe assembly 130 can retract the saline plunger 146 as the medication plunger 156 is advanced to receive or draw the displaced fluid from the IV tubing. As previously described, during a priming operation, the medication gear rack 158 and the saline gear rack 148 can be in meshed engagement with the connecting gear 172. Therefore, during operation, as the medication plunger 156 is advanced or pushed downward, the medication gear rack 158 rotates the connecting gear 172 in a clockwise direction. The rotation of the connecting gear 172 retracts the saline gear rack 148 and therefore the saline plunger 146. By retracting the saline plunger 146, saline or other displaced medical fluids can be drawn from the IV tubing.

Figure 8:
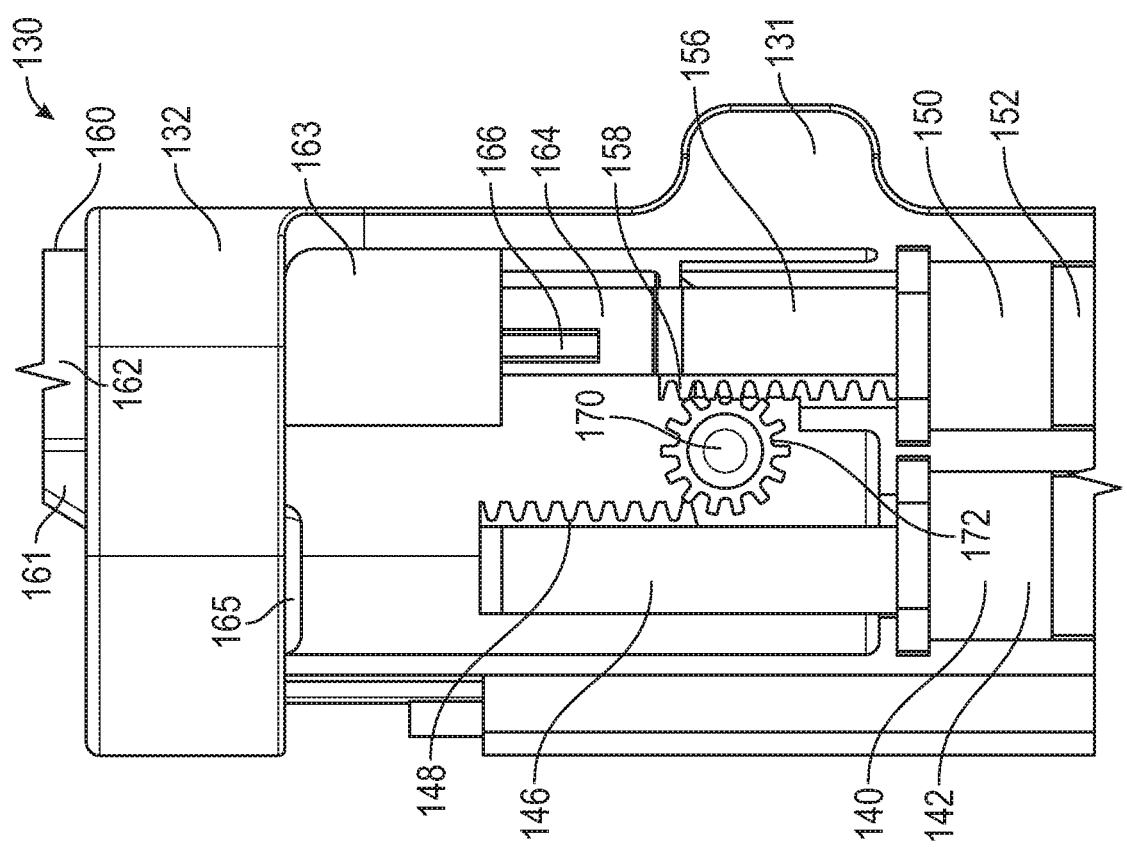
FIG. 8 is a detail view of the syringe assembly of FIG. 5 in a delivery configuration, in accordance with various aspects of the present disclosure.

FIG. 8 is a detail view of the syringe assembly 130 of FIG. 5 in a delivery configuration, in accordance with various aspects of the present disclosure. At the end of the priming sequence, the saline gear rack 148 of the saline plunger 146 is disengaged from the connecting gear 172, allowing the saline plunger 146 and the medication plunger 156 to move independently after priming.

Figure 9:
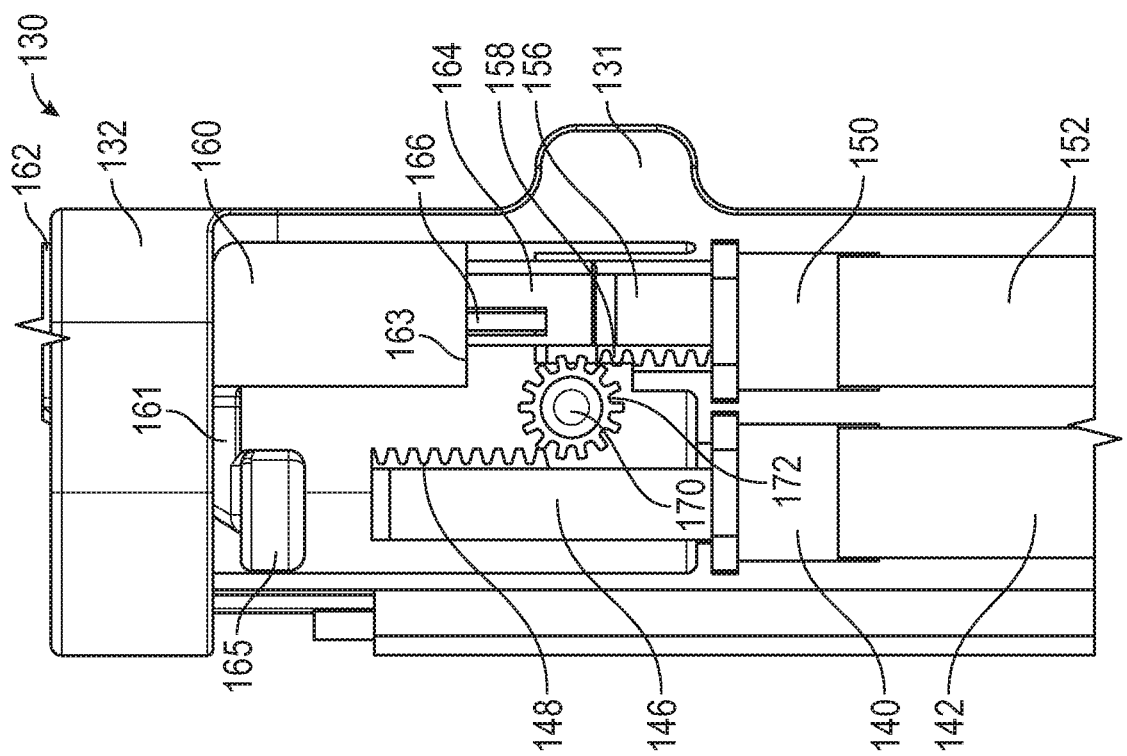
FIG. 9 is a detail view of the syringe assembly of FIG. 5 in the delivery configuration, in accordance with various aspects of the present disclosure.

FIG. 9 is a detail view of the syringe assembly 130 of FIG. 5 in the delivery configuration, in accordance with various aspects of the present disclosure. After priming, the pusher assembly 160 can be further advanced to administer medication to the patient.

In the illustrated embodiment, by further advancing the pusher assembly 160, the main pusher shaft 162 and the intermediate pusher shaft 164 cooperatively advance the medication plunger 156 to administer medication to the patient.

Figure 10:
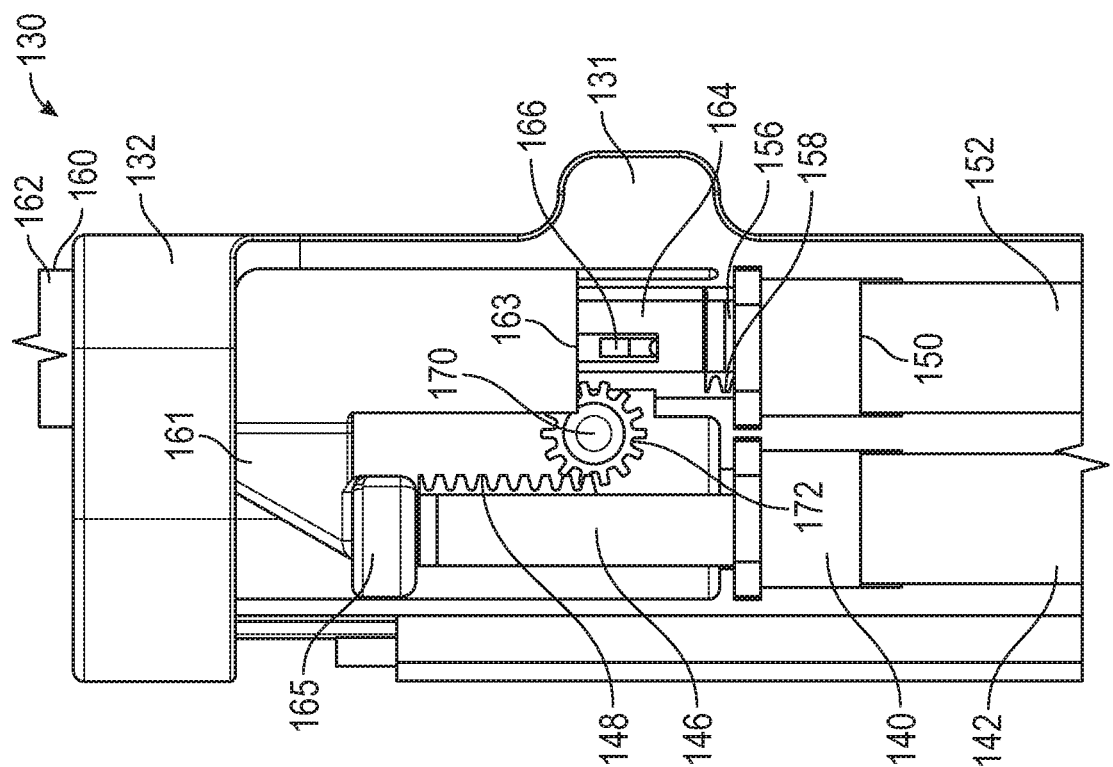
FIG. 10 is a detail view of the syringe assembly of FIG. 5 in a pushing configuration, in accordance with various aspects of the present disclosure.

FIG. 10 is a detail view of the syringe assembly 130 of FIG. 5 in a pushing configuration, in accordance with various aspects of the present disclosure. During operation, the pusher assembly 160 can be further advanced to deliver any remaining medication in the IV tubing to the patient.

By advancing the pusher assembly 160, the secondary pusher 165 engages and advances the saline plunger 146. By advancing the saline plunger 146, saline can be administered from the saline syringe 140 into the IV tubing to "push" or deliver any remaining medication in the IV tubing to the patient. As described herein, the secondary pusher 165 can be longitudinally offset from the intermediate pusher shaft 164 to allow the secondary pusher 165 to actuate the saline plunger 146 after the medication plunger 156 is actuated.

After the medication plunger 156 reaches the end of its desired travel, the intermediate pusher shaft 164 is preferably disengaged from the main pusher shaft 162 to allow the pusher assembly 160 to be advanced without obstruction or further advancing the medication plunger 156. Advantageously, by disengaging the intermediate pusher shaft 164, the pusher assembly 160 can advance the offset secondary pusher 165 and the saline plunger 146 after advancing the medication plunger 156.

Figure 11:
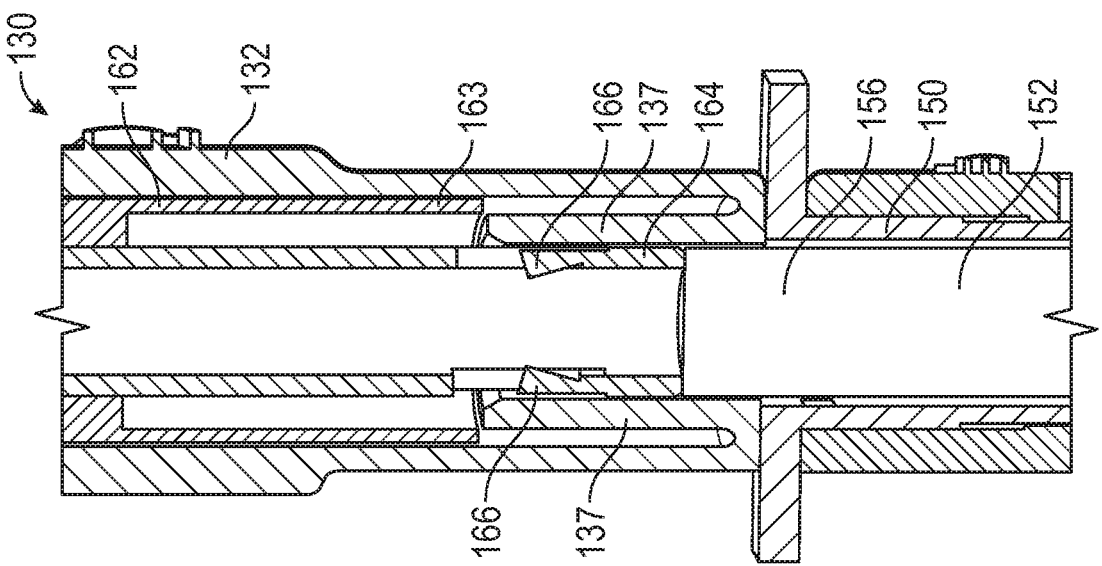
FIG. 11 is a partial cross-sectional view of the syringe assembly of FIG. 5, in accordance with various aspects of the present disclosure.

FIG. 11 is a partial cross-sectional view of the syringe assembly 130 of FIG. 5, in accordance with various aspects of the present disclosure. With reference to FIGS. 10 and 11, in some embodiments, the intermediate pusher shaft 164 enters the activation tunnel 137 to release the intermediate pusher shaft 164 from the main pusher shaft 162 as the medication plunger 156 reaches the end of travel. As illustrated, as the intermediate pusher shaft 164 enters the activation tunnel 137 the ears 166 of the intermediate pusher shaft 164 can be radially retracted or compressed by the walls of the activation tunnel 137. After the ears 166 of the intermediate pusher shaft 164 are retracted, the intermediate pusher shaft 164 is uncoupled from the main pusher shaft 162, permitting the main pusher shaft 162 to continue advancing to without further actuating the medication plunger 156. As illustrated, the intermediate pusher shaft 164 can retract or slide into the inner diameter of the main pusher shaft 162.

Figure 12:
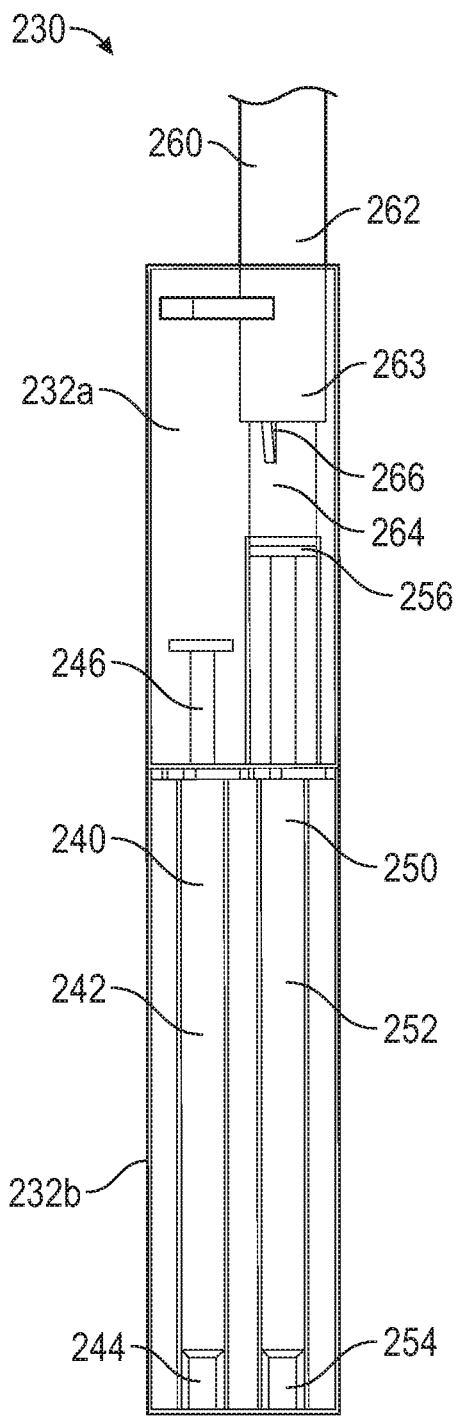
FIG. 12 is an elevation view of a syringe assembly, in accordance with various aspects of the present disclosure.
Figure 13:
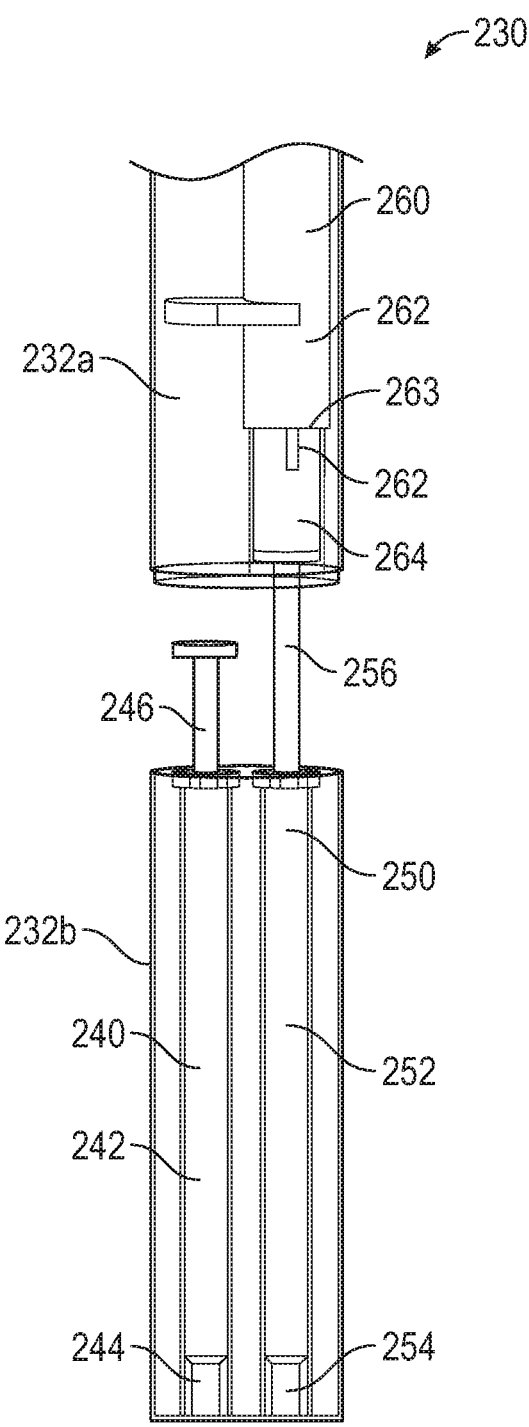
FIG. 13 is an elevation view of the syringe assembly of FIG. 12 in an open configuration, in accordance with various aspects of the present disclosure.

FIG. 12 is an elevation view of a syringe assembly 230, in accordance with various aspects of the present disclosure. FIG. 13 is an elevation view of the syringe assembly 230 of FIG. 12 in an open configuration, in accordance with various aspects of the present disclosure. In some embodiments, the syringe assembly 230 can include features that are similar to syringe assembly 130. Unless otherwise noted, similar features may be referred to with similar reference numerals.

With reference to FIGS. 12 and 13, the syringe assembly 230 includes a top portion 232a and a bottom portion 232b that separate to allow a saline syringe 240 and a medication syringe 250 to be introduced or removed from the syringe assembly 230. The top portion 232a and the bottom portion 232b can be assembled to facilitate operation.

Advantageously, a multi-portion syringe assembly 230 allows clinicians to easily introduce and remove syringes from the syringe assembly 230. Further, the multi-portion syringe assembly 230 can allow for premade or commercial syringes to be used with the syringe assembly 230. In some embodiments, the syringe assembly 230 allows for pre-filled syringes to be used.

The present disclosure is provided to enable any person skilled in the art to practice the various aspects described herein. The disclosure provides various examples of the subject technology, and the subject technology is not limited to these examples. Various modifications to these aspects will be readily apparent to those skilled in the art, and the generic principles defined herein may be applied to other aspects.

A reference to an element in the singular is not intended to mean "one and only one" unless specifically so stated, but rather "one or more." Unless specifically stated otherwise, the term "some" refers to one or more. Pronouns in the masculine (e.g., his) include the feminine and neuter gender (e.g., her and its) and vice versa. Headings and subheadings, if any, are used for convenience only and do not limit the invention.

The word "exemplary" is used herein to mean "serving as an example or illustration." Any aspect or design described herein as "exemplary" is not necessarily to be construed as preferred or advantageous over other aspects or designs. In one aspect, various alternative configurations and operations described herein may be considered to be at least equivalent.

A phrase such as an "aspect" does not imply that such aspect is essential to the subject technology or that such aspect applies to all configurations of the subject technology. A disclosure relating to an aspect may apply to all configurations, or one or more configurations. An aspect may provide one or more examples. A phrase such as an aspect may refer to one or more aspects and vice versa. A phrase such as an "embodiment" does not imply that such embodiment is essential to the subject technology or that such embodiment applies to all configurations of the subject technology. A disclosure relating to an embodiment may apply to all embodiments, or one or more embodiments. An embodiment may provide one or more examples. A phrase such an embodiment may refer to one or more embodiments and vice versa. A phrase such as a "configuration" does not imply that such configuration is essential to the subject technology or that such configuration applies to all configurations of the subject technology. A disclosure relating to a configuration may apply to all configurations, or one or more configurations. A configuration may provide one or more examples. A phrase such a configuration may refer to one or more configurations and vice versa.

In one aspect, unless otherwise stated, all measurements, values, ratings, positions, magnitudes, sizes, and other specifications that are set forth in this specification, including in the claims that follow, are approximate, not exact. In one aspect, they are intended to have a reasonable range that is consistent with the functions to which they relate and with what is customary in the art to which they pertain.

In one aspect, the term "coupled" or the like may refer to being directly coupled. In another aspect, the term "coupled" or the like may refer to being indirectly coupled.

Terms such as "top," "bottom," "front," "rear" and the like if used in this disclosure should be understood as referring to an arbitrary frame of reference, rather than to the ordinary gravitational frame of reference. Thus, a top surface, a bottom surface, a front surface, and a rear surface may extend upwardly, downwardly, diagonally, or horizontally in a gravitational frame of reference.

Various items may be arranged differently (e.g., arranged in a different order, or partitioned in a different way) all without departing from the scope of the subject technology. All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112, sixth paragraph, unless the element is expressly recited using the phrase "means for" or, in the case of a method claim, the element is recited using the phrase "step for." Furthermore, to the extent that the term "include," "have," or the like is used, such term is intended to be inclusive in a manner similar to the term "comprise" as "comprise" is interpreted when employed as a transitional word in a claim.

The Title, Background, Summary, Brief Description of the Drawings and Abstract of the disclosure are hereby incorporated into the disclosure and are provided as illustrative examples of the disclosure, not as restrictive descriptions. It is submitted with the understanding that they will not be used to limit the scope or meaning of the claims. In addition, in the Detailed Description, it can be seen that the description provides illustrative examples and the various features are grouped together in various embodiments for the purpose of streamlining the disclosure. This method of disclosure is not to be interpreted as reflecting an intention that the claimed subject matter requires more features than are expressly recited in each claim. Rather, as the following claims reflect, inventive subject matter lies in less than all features of a single disclosed configuration or operation. The following claims are hereby incorporated into the Detailed Description, with each claim standing on its own as a separately claimed subject matter.

The claims are not intended to be limited to the aspects described herein, but is to be accorded the full scope consistent with the language claims and to encompass all legal equivalents. Notwithstanding, none of the claims are intended to embrace subject matter that fails to satisfy the requirement of 35 U.S.C. § 101, 102, or 103, nor should they be interpreted in such a way.

What is claimed is:

1. A syringe assembly, comprising:
   an assembly housing;
   a first syringe disposed within the assembly housing, the first syringe comprising:
      a first syringe body defining a first syringe cavity and a first syringe port, wherein the first syringe port is in fluid communication with the first syringe cavity; and
      a first plunger movable within the first syringe cavity and defining a first chamber in the first syringe cavity, wherein the first chamber is in fluid communication with the first syringe port, the first plunger comprising a first gear rack extending longitudinally along the first plunger;
   a second syringe disposed within the assembly housing, the second syringe comprising:
      a second syringe body defining a second syringe cavity and a second syringe port, wherein the second syringe port is in fluid communication with the second syringe cavity; and
      a second plunger movable within the second syringe cavity and defining a second chamber in the second syringe cavity, wherein the second chamber is in fluid communication with the second syringe port, the second plunger comprising a second gear rack extending longitudinally along the second plunger;
   a connecting gear rotatably coupled to the assembly housing, wherein the connecting gear is configured to be in meshed engagement with at least one of the first gear rack and the second gear rack; and
   a pusher assembly moveable within the assembly housing, the pusher assembly comprising:
      a main pusher shaft extending from outside of the assembly housing to inside the assembly housing; and
      an intermediate pusher shaft releasably coupled to the main pusher shaft, wherein the intermediate pusher shaft is configured to engage with and advance the first plunger.

2. The syringe assembly of claim 1, wherein the connecting gear is configured to be in meshed engagement with the first gear rack and the second gear rack in a priming configuration.

3. The syringe assembly of claim 2, wherein the second plunger is movable within the second syringe cavity in an opposite direction to the first plunger within the first syringe cavity in the priming configuration.

4. The syringe assembly of claim 1, wherein the connecting gear is configured to be in meshed engagement with the first gear rack in a delivery configuration.

5. The syringe assembly of claim 1, wherein the connecting gear is configured to be in meshed engagement with the second gear rack in a pushing configuration.

6. The syringe assembly of claim 1, wherein the intermediate pusher shaft extends from a main pusher shaft end of the main pusher shaft.

7. The syringe assembly of claim 6, wherein the intermediate pusher shaft comprises a plurality of ears extending radially from the intermediate pusher shaft, wherein the plurality of ears engage the main pusher shaft end to releasably couple the intermediate pusher shaft to the main pusher shaft.

8. The syringe assembly of claim 7, wherein the assembly housing comprises an activation tunnel disposed around the first plunger, wherein the activation tunnel is configured to radially compress the plurality of ears to disengage the plurality of ears from the main pusher shaft end to permit the intermediate pusher shaft to move relative to the main pusher shaft.

9. The syringe assembly of claim 1, the pusher assembly further comprising: a second pusher configured to engage with and advance the second plunger; and a second pusher extension coupling the second pusher to the main pusher shaft.

10. The syringe assembly of claim 1, wherein the assembly housing comprises a hinged cover, wherein the hinged cover can releasably enclose the first syringe, the second syringe, and the connecting gear in a closed configuration.

11. The syringe assembly of claim 10, wherein the hinged cover comprises a first window, wherein the first window is at least partially aligned with the first syringe body in the closed configuration.

12. The syringe assembly of claim 1, further comprising a cover configured to rotate about one or more hinges relative to the assembly housing to permit access to the first syringe and the second syringe within the assembly housing.

13. A medication delivery system, comprising:
   a syringe assembly, comprising:
      an assembly housing;
      a first syringe disposed within the assembly housing, the first syringe comprising:
         a first syringe body defining a first syringe cavity and a first syringe port, wherein the first syringe port is in fluid communication with the first syringe cavity; and
         a first plunger movable within the first syringe cavity and defining a first chamber in the first syringe cavity, wherein the first chamber is in fluid communication with the first syringe port, the first plunger comprising a first gear rack extending longitudinally along the first plunger;
      a second syringe disposed within the assembly housing, the second syringe comprising:
         a second syringe body defining a second syringe cavity and a second syringe port, wherein the second syringe port is in fluid communication with the second syringe cavity; and a second plunger movable within the second syringe cavity and defining a second chamber in the second syringe cavity, wherein the second chamber is in fluid communication with the second syringe port, the second plunger comprising a second gear rack extending longitudinally along the second plunger; and a connecting gear rotatably coupled to the assembly housing, wherein the connecting gear is configured to be in meshed engagement with at least one of the first gear rack and the second gear rack;

a pusher assembly moveable within the assembly housing, the pusher assembly comprising:

a main pusher shaft extending from outside of the assembly housing to inside the assembly housing; and an intermediate pusher shaft releasably coupled to the main pusher shaft, wherein the intermediate pusher shaft is configured to engage with and advance the first plunger; and a tubing defining a first flow path and a second flow path, wherein the first flow path is in fluid communication with the first syringe port, and the second flow path is in fluid communication with the second syringe port.

14. The medication delivery system of claim 13, further comprising a flow delivery line in fluid communication between the second syringe port and the first flow path.

\* \* \* \* \*